(12) United States Patent
Mukhopadhyay et al.

(10) Patent No.: US 9,079,818 B2
(45) Date of Patent: Jul. 14, 2015

(54) PROCESS FOR SYNTHESIS OF FLUORINATED OLEFINS

(75) Inventors: Sudip Mukhopadhyay, Berkeley, CA (US); Cheryl L. Bortz, North Tonawanda, NY (US); Barbara A. Light, Niagara Falls, NY (US); Cheryl L. Cantlon, Clarence Center, NY (US); Robert C. Johnson, Lancaster, NY (US)

(73) Assignee: HONEYWELL INTERNATIONAL INC., Morristown, NJ (US)

( * ) Notice: Subject to any disclaimer, the term of this patent is extended or adjusted under 35 U.S.C. 154(b) by 1339 days.

(21) Appl. No.: 12/249,958

(22) Filed: Oct. 12, 2008

(65) Prior Publication Data

US 2009/0099396 A1    Apr. 16, 2009

Related U.S. Application Data

(60) Provisional application No. 61/068,509, filed on Oct. 15, 2007.

(51) Int. Cl.

| C07C 21/00 | (2006.01) |
|---|---|
| C07C 17/00 | (2006.01) |
| C07C 17/21 | (2006.01) |
| C07C 17/23 | (2006.01) |
| C07C 17/25 | (2006.01) |
| C07C 21/18 | (2006.01) |

(52) U.S. Cl.
CPC ............. *C07C 17/21* (2013.01); *C07C 17/23* (2013.01); *C07C 17/25* (2013.01); *C07C 21/18* (2013.01)

(58) Field of Classification Search
CPC combination set(s) only.
See application file for complete search history.

(56) References Cited

U.S. PATENT DOCUMENTS

| 2,931,840 | A | 4/1960 | Marquis et al. |
|---|---|---|---|
| 4,900,874 | A | 2/1990 | Ihara et al. |
| 5,162,594 | A | 11/1992 | Krespan |
| 5,986,151 | A | 11/1999 | Van Der Puy |
| 6,124,510 | A | 9/2000 | Elsheikh et al. |
| 6,548,719 | B1 | 4/2003 | Nair et al. |
| 2003/0060669 | A1 * | 3/2003 | Shibata et al. ............ 570/136 |
| 2007/0112230 | A1 * | 5/2007 | Mukhopadhyay et al. ... 570/161 |
| 2007/0197842 | A1 | 8/2007 | Mukhopadhyay |
| 2009/0030247 | A1 | 1/2009 | Johnson et al. |
| 2009/0203945 | A1 | 8/2009 | Mukhopadhyay et al. |

FOREIGN PATENT DOCUMENTS

| WO | 2007019355 | 2/2007 |
|---|---|---|
| WO | 2007053736 | 5/2007 |

OTHER PUBLICATIONS

R. Banks et al., Preparation of 2,3,3,3-Tetrafluoropropene From Trifluoroacetylacetone and Sulphur Tetrafluoride, Journal of Fluorine Chemistry, 1997, 171-174, 82, United Kingdom.

* cited by examiner

*Primary Examiner* — Clinton Brooks
(74) *Attorney, Agent, or Firm* — Bruce Bradford

(57) ABSTRACT

Disclosed is a process for the synthesis of fluorinated olefins, and in particularly preferred embodiments tetrafluorinated olefins having F on an unsaturated, non-terminal carbon, such as 2,3,3,3-tetrafluoropropene. The preferred processes of the present invention in accordance with one embodiment generally comprise:

(a) reacting a compound of formula (I)

$$X^1X^2 \qquad (I)$$

with a compound of formula (II)

$$CX^1X^2X^3CX^1{=}CX^1X^2 \qquad (II)$$

to produce a reaction product comprising a compound of formula (III)

$$CF_3CHX^1CH_2X^2 \qquad (III), \text{ and}$$

(b) exposing said compound of formula (III) to reaction conditions effective to convert said compound of formula (III) to a compound of formula (IV)

$$CF_3CZ{=}CH_2 \qquad (IV)$$

wherein $X^1$, $X^2$, and $X^3$ are each independently selected from the group consisting of hydrogen, chlorine, bromine, fluorine and iodine, provided that $X^1$ and $X^2$ in formula (I) are not both hydrogen and Z is Cl, I, Br, or F.

12 Claims, No Drawings

PROCESS FOR SYNTHESIS OF FLUORINATED OLEFINS

CROSS REFERENCE TO RELATED APPLICATIONS

This application claims the priority benefit of U.S. Provisional Application No. 60/068,509, filed Oct. 15, 2007, which is incorporated herein by reference.

FIELD OF THE INVENTION

The present invention relates to methods for the preparation of fluorinated olefins, and in particular tetrafluorinated propenes. In specific embodiments, the invention concerns processes for the preparation of 2,3,3,3-tetrafluoropropene, $CF_3CF=CH_2$ (HFO-1234yf).

BACKGROUND

Hydrofluorocarbons (HFC's), in particular hydrofluoroalkenes (i.e. hydrofluoroolefins (HFOs)) such as tetrafluoropropenes (including 2,3,3,3-tetrafluoro-1-propene (HFO-1234yf)) have been disclosed to be effective refrigerants, fire extinguishants, heat transfer media, propellants, foaming agents, blowing agents, gaseous dielectrics, sterilant carriers, polymerization media, particulate removal fluids, carrier fluids for buffing abrasive agents, displacement drying agents and power cycle working fluids. Unlike chlorofluorocarbons (CFCs) and hydrochlorofluorocarbons (HCFCs), both of which potentially damage the Earth's ozone layer, HFCs do not contain chlorine and, thus, pose no threat to the ozone layer. However, compared to HFCs, HFOs are generally even more ecologically friendly because they generally have a lower Global Warming Potential (GPW).

Several methods for preparing hydrofluoroalkanes are known. For example, U.S. Pat. No. 4,900,874 describes a method of making fluorine containing olefins by contacting hydrogen gas with fluorinated alcohols. U.S. Pat. No. 2,931,840 describes a method of making fluorine containing olefins by pyrolysis of methyl chloride and tetrafluoroethylene or chlorodifluoromethane. The preparation of HFO-1234yf from trifluoroacetylacetone and sulfur tetrafluoride has been described. See Banks, et al., Journal of Fluorine Chemistry, Vol. 82, Iss. 2, p. 171-174 (1997). Also, U.S. Pat. No. 5,162,594 discloses a process wherein tetrafluoroethylene is reacted with another fluorinated ethylene in the liquid phase to produce a polyfluoroolefin product.

U.S. Pat. No. 6,548,719 describes generally the production of a wide range of fluoroolefins by dehydrohalogenating, in the presence of a phase transfer catalyst, a compound of formula $CF_3C(R^1_aR^2_b)C(R^3_cR^4_d)$ with at least one alkali metal hydroxide, where the R substituents are as defined in the patent, provided that there is at least one hydrogen and one halogen on adjacent carbon atoms.

The preparation of 1,3,3,3-tetrafluoropropene is disclosed in U.S. Pat. No. 5,986,151 and U.S. Pat. No. 6,124,510. These patents disclose processes that comprise catalytic dehydrofluorination of $CF_3CH_2CF_2H$ in the gas phase to afford $CF_3CH=CHF$. However, each of these methods has the disadvantage of being limited by the requirement of isolating 1,1,1,3,3-pentafluoropropane ("245fa") as a starting reactant, which may be undesirable for reasons including cost and material availability.

SUMMARY OF THE INVENTION

Applicants have discovered a process for the synthesis of fluorinated olefins, and in particularly preferred embodiments, tetrafluorinated olefins having F on an unsaturated, non-terminal carbon, such as 2,3,3,3-tetrafluoropropene.

The preferred processes of the present invention in accordance with one embodiment generally comprise:
(a) reacting a compound of formula (I)

$$X^1X^2 \qquad (I)$$

with a compound of formula (II)

$$CX^1X^2X^3CX^1=CX^1X^2 \qquad (II)$$

to produce a reaction product comprising a compound of formula (III)

$$CF_3CHX^1CH_2X^2 \qquad (III), and$$

(b) exposing said compound of formula (III) to reaction conditions effective to convert said compound of formula (III) to a compound of formula (IV)

$$CF_3CZ=CH_2 \qquad (IV)$$

wherein $X^1$, $X^2$, and $X^3$ are each independently selected from the group consisting of hydrogen, chlorine, bromine, fluorine and iodine, provided that $X^1$ and $X^2$ in formula (I) are not both hydrogen and that Z is Cl, I, Br, or F.

In specifically preferred embodiments directed to the formation of 1,3,3,3-tetrafluoropropene (HFO-1234yf), the processes comprise:
(a) reacting a compound of formula (IA)

$$X^1X^2 \qquad (IA)$$

with a compound of formula (IIA)

$$CH_2X^2CX^2=CX^2X^2 \qquad (IIA)$$

to produce a reaction product comprising a compound of formula (IIIA)

$$CF_3CHFCH_2Cl \qquad (IIIA), and$$

(b) exposing said compound of formula (IIIA) to reaction conditions effective to convert said compound of formula (IIIA) to a compound of formula (IVA)

$$CF_3CF=CH_2 \qquad (IVA)$$

wherein $X^1$ is selected from the group consisting of hydrogen, chlorine, bromine, fluorine and iodine, and each $X^2$ is each independently selected from the group consisting of chlorine, bromine, fluorine and iodine.

In certain highly preferred embodiments, the compound of formula (I) comprises HF, the compound of formula (II) comprises $CCl_2=CClCH_2Cl$ (HFCO-1230), and the compound of formula (III) comprises $CF_3CHFCH_2F$ (HFC-245eb).

The present invention is, thus, directed to processes which involve, in one embodiment, the production of $CF_3CF=CH_2$ and which are amenable to scale up from readily available and relatively inexpensive starting materials.

DETAILED DESCRIPTION OF PREFERRED EMBODIMENTS

The present invention is directed, in preferred embodiments, to methods for the production of 2,3,3,3-tetrafluoropropene, $CF_3CF=CH_2$ ("HFO-1234yf").

The step of reacting a compound of formula (I), including compounds of formula (IA) (preferably HF), with a compound of formula (II), including compounds of formula (IIA) (preferably HFCO-1230), is amenable to a large number of specific processing condition and steps in accordance with the teachings contained herein, and all such variations are within the broad scope of the present invention. For example, the reaction step (a) may comprise a liquid-phase or a gas-phase addition reaction, either catalyzed or uncatalyzed, although catalyzed liquid-phase reactions are generally preferred.

For embodiments in which the compound of formula (I) comprises HF and the compound of formula (II) comprises a compound of formula (IIA), and more preferably HFCO-1230, it is preferred that the reaction step comprises exposing the reactants, preferably at a temperature of from about 0° C. to about 250° C., and even more preferably at a temperature of from about 150° C. to about 250° C., in the presence of a catalyst, preferably a halide of a metal selected from period 5, groups 10 through 15. Highly preferred catalyst comprises, and preferably comprises in major proportion, one or more halides of antimony, preferably $SbCl_5$.

It is contemplated that numerous and varied other reaction conditions may be used for the reaction step (a). For example, the reaction pressure may vary widely, but in preferred embodiments the reaction occurs under pressure, preferably pressure of at least about 500 psig of pressure, more preferably at pressures of from about 500 to about 1000 psig, and even more preferably at pressures of from about 700 to about 1000 psig. Furthermore, for batch reaction conditions in particular, it is contemplated that the reaction time is from about 5 hours to about 24 hours, more preferably from about 5 hours to about 15 hours.

Preferably, the reaction step (a) produces a reaction product comprising a compound of formula (III), more preferably formula (IIIA), and even more preferably HFCO-1230. In preferred embodiments, the conversion of the compound of formula II in the reaction is from about 70% to about 100% and the selectivity of the reaction to formula (III) compounds, more preferably formula (IIIA) compounds, and even more preferably HFC-245eb, is from about 40% to about 70%. In certain preferred embodiments the reaction product also contains, in addition to the preferred HFC-245eb, $CF_3CHFCH_2Cl$ (HCFC-244), $CF_3CHClCH_2Cl$ (HCFC-243), $CF_3CHClCH_2F$ (HCFC-244), $CF_3CCl=CH_2$, (HFCO-1233), $CF_3CFClCH_3$ (HCFC-244), and tar.

Optionally, but preferably, the reaction product from the reaction step (a) is subjected to one or more separation steps, including preferably distillation, to produce a product having a relatively higher concentration of compounds of formula (III), and even more preferably compounds of formula (IIIA), for use as a feed material to the exposing step (b). In certain preferred embodiments, the concentration of formula (III) compounds (exclusive of carrier fluid or other inert components) is at least about 90%, and even more preferably at least about 95%, by weight.

After the reaction step (a), the reaction product, or at least a portion thereof, with or without fractionation, is preferably exposed to reaction conditions effective to produce a reaction product comprising at least one compound of formula (IV), more preferably formula (IVA), and even more preferably 2,3,3,3-tetrafluoropropene (HFO-1234yf). In preferred embodiments, the exposing step comprises dehydrohalogenating the compound of formula (III), in the gas and/or liquid phase. Although it is contemplated that numerous dehydrohalogenation steps can be utilized with good effect in accordance with the teachings contained herein, it is preferred in certain embodiments that the dehydrohalogentaion step comprises contacting the compound of formula (III), in the liquid phase with a potassium hydroxide solution, in the presence, or not, of Crown ether, or in the gas phase with a catalyst, at a relatively elevated temperature for a time sufficient to convert the compound to 2,3,3,3-tetrafluoropropene.

For embodiments involving the preferred liquid phase dehyrdofluorination, it is generally preferred that the compound of formula (III) is reacted in aqueous KOH in a concentration of from about 10% to about 35%, preferably from about 20% to about 25%, at temperatures of from about 25° C. to about 90° C., and more preferably from about 45° C. to about 80° C.

It is contemplated that numerous and varied other reaction conditions may be used for the liquid phase dehydrohalogenation. For example, the reaction pressure may vary widely, but in preferred embodiments the reaction occurs, at least in part, under pressure, preferably a pressure of at least about 100 psig, more preferably a pressure from about 150 psig to about 200 psig, and even more preferably a pressure of from about 150 to about 180 psig. Furthermore, particularly for batch reaction conditions, it is contemplated that the reaction time is from about 5 hours to about 24 hours, more preferably from about 15 hours to about 25 hours.

Preferred gas phase dehydrohalogenation reactions comprise introducing a stream containing the compound of formula (III) into a reactor which preferably contains a catalyst, preferably a bed of metal-based catalyst, more preferably Pd or Ni on carbon, maintained at temperature of from about 200° C. to about 500° C., and even more preferably at temperatures of from about 250° C. to about 500° C.

It may be possible in certain embodiments to utilize an exposing step conducted in accordance with the teachings of U.S. Pat. No. 6,548,719, which is assigned to the assignee of the present invention and which is incorporated herein by reference. Gas phase dehydrofluorination with an appropriate catalyst and at elevated temperature may also be performed in certain embodiments in accordance with the procedures as described in U.S. Pat. No. 5,986,151, which is also incorporated herein by reference.

The exposing step preferably produces a reaction product stream which comprises tetrafluoropropene, and in particular 2,3,3,3-tetrafluoropropene (HFO-1234yf). In preferred embodiments, the conversion of the compound of formula III in the dehydrohalogenation reaction is from about 70% to about 100% and the selectivity of the reaction for formula (IV), and for HFO-1234yf in particular, is from about 70 to about 95%, more preferably from about 80 to 95%.

Optionally, but preferably, the reaction product from the exposing step (b) is subjected to one or more separation steps, including preferably distillation, to produce a product having a relatively higher concentration of compounds of formula (IV), more preferably compounds of formula (IV), and even more preferably HFO-1234yf. In certain preferred embodiments, the concentration of formula (IV) compounds (exclusive of carrier fluid or other inert components) is at least about 90%, and even more preferably at least about 95%, by weight.

EXAMPLES

Example 1

Synthesis of $CF_3CHFCH_2F$ (245eb) by Liquid-Phase Catalytic Reaction of $CCl_2=CClCH_2Cl$ with HF 350 grams HF and 50 grams $CCl_2=CClCH_2Cl$ were charged into a 1-L teflon-lined, Monel autoclave. The reaction mixture was stirred at 100° C. and when the temperature reaches to 100° C., 75 grams $SbCl_5$ was added into the reaction mixture. The mixture was stirred for 12 hours under 625 psig of pressure. After the reaction, the reactor was cooled to room temperature and 300 ml water was then added slowly into the autoclave over a period of 45 min. After complete addition of water under stirring, the reactor was cooled to room temperature and then the overhead gases were transferred to another collecting cylinder. The yield of $CF_3CHFCH_2F$ was 53% at a $CCl_2$=$CClCH_2Cl$ conversion level of about 100%. The other major by-products were $CF_3CHFCH_2Cl$, $CF_3CHClCH_2F$, $CF_3CHClCH_2Cl$, $CF_3CCl$=$CH_2$, $CF_3CFClCH_3$, and an unidentified isomer. The desired product, $CF_3CHFCH_2F$ was isolated by distillation with 99% purity.

Example 2

Synthesis of $CF_3CHFCH_2F$ (245eb) by Liquid-Phase Catalytic Reaction of $CCl_2$=$CClCH_2Cl$ with HF 350 grams HF, 50 grams $CCl_2$=$CClCH_2Cl$ and 75 grams $SbCl_5$ were charged into a 1-L teflon-lined, Monel autoclave. The reaction mixture was stirred at 125° C. for 12 h under 743 psig of pressure. After the reaction, the reactor was cooled to room temperature and 300 ml water was then added slowly into the autoclave over a period of 45 min. After complete addition of water under stirring, the reactor was cooled to room temperature and then the overhead gases were transferred to another collecting cylinder. The yield of $CF_3CHFCH_2F$ was 57% at a $CCl_2$=$CClCH_2Cl$ conversion level of about 100%. The other major by-products were $CF_3CHFCH_2Cl$, $CF_3CHClCH_2Cl$, $CF_3CHClCH_2F$, $CF_3CCl$=$CH_2$, $CF_3CFClCH_3$, and tar. The desired product, $CF_3CHFCH_2F$ was isolated by distillation with 99% purity.

Example 3

Synthesis of $CF_3CHFCH_2F$ (245eb) by Liquid-Phase Catalytic Reaction of $CCl_2$=$CClCH_2Cl$ with HF 350 g HF, 50 g $CCl_2$=$CClCH_2Cl$, and 75 g $SbCl_5$ were charged into a 1-L autoclave. The reaction mixture was stirred at 150° C. for 8 h under 910 psig of pressure. After the reaction, the reactor was cooled to room temperature and 300 ml water was then added slowly into the autoclave over a period of 45 min. After complete addition of water under stirring, the reactor was cooled to room temperature and then the overhead gases were transferred to another collecting cylinder. The yield of $CF_3CHFCH_2F$ was 59% at a $CCl_2$=$CClCH_2Cl$ conversion level of about 100%. The other major by-products were mostly polymers and tars.

Example 4

Synthesis of $CF_3CF$=$CH_2$ (HFO-1234yf) by Gas-Phase Reaction of $CF_3CHFCH_2F$ 1.32 Kg (9.85 mol) $CF_3CHFCH_2F$ (99% pure) is stirred with 2.5 L (10.1 mol) of 25% KOH solution in the presence or absence of 18-Crown ether at 50° C. Without being bound to theory, the reaction is believed proceed as indicated below:

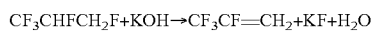
$CF_3CHFCH_2F+KOH \rightarrow CF_3CF$=$CH_2+KF+H_2O$

A cleaned and leak tested 2 gallon autoclave was evacuated and then 2.5 L KOH water solution as indicated above was charged into it. The KOH solution was cooled down to 0° C. by chiller. The autoclave was evacuated again and using vacuum, 1.32 Kg $CF_3CFHCFH_2$ was then charged into it. The sealed reactor was gradually heated with stirring to 55° C. and then was heated by setting temperature at 55° C. After a reaction time of about 45 min., the temperature increased to 70° C. by exothermic reaction (pressure was 165 psig). A 0° C. cooling liquid was applied to bring the temperature down to 57° C. Then the reaction was continued at 55° C. for 20 h.

The reaction mixture was cooled down to 30° C. and the gas product was transferred into a cylinder at dry ice-acetone temperature. 1.1 Kg $CF_3CF$=$CH_2$ with GC purity 98.6% was collected.

Example 5

Synthesis of $CF_3CF$=$CH_2$ (HFO-1234yf) by Gas-Phase Reaction of $CF_3CHFCH_2F$, $CF_3CHFCH_2Cl$, and $CF3CHClCH_2F$ In a gas phase dehydrohalogenation reaction, 50 sccm $CF_3CHFCH_2F$ was passed over a 100 cc catalyst bed comprised of $Cr_2O_3$ or Ni-mesh or activated carbon or Pd/C or Ni/C kept inside a monel reactor in the presence of 20 sccm of HF at 250-400° C. to synthesize $CF_3CF$=$CH_2$ which was finally trapped in a dry ice tap. The results using different catalysts are shown in Table 1.

In a typical reaction, a 22-inch long monel reactor with ½-inch inner diameter was charged with 100 cc catalyst. A flow of 20 sccm of $N_2$ was always kept during the reaction. The reactor temperature was then raised gradually to the desired reaction temperature. HFC-245eb was passed through gas-flow controllers into a preheater. The preheater temperature was kept at 300° C. The gas stream coming out of the preheater was passed through the catalyst bed at the desired temperature over a specified period of time. An on-line GC and a GCMS were used to analyze samples taken at the reactor exit line at regular time intervals. Finally, the reactor exit stream was run into a 20% KOH scrubber solution at room temperature to eliminate any acid HF formed in-situ during the reaction. The exit gas mixture coming out of the scrubber solution was then condensed in a dry-ice trap to collect the products. The desired product $CF_3CF$=$CH_2$ (1234yf) was then isolated from the mixture by distillation. Results are shown in Table 1

TABLE 1

| Dehydrofluorination of 245eb different heterogeneous catalysts | | | | |
|---|---|---|---|---|
| # | Catalyst | 245eb flow rate, g/h | T° C. | Conversion of 245eb | Selectivity for 1234yf |
| 1A | Ni-mesh | 10 | 495 | 36 | 100 |
| 1B | Ni-mesh | 10 | 525 | 67 | 100 |
| 1C | Ni-mesh | 10 | 565 | 89 | 78 |
| 2A | 2-wt % Ni/C | 10 | 495 | 63 | 94 |
| 2B | 2-wt % Ni/C | 10 | 525 | 79 | 84 |
| 2C | 2-wt % Ni/C | 8 | 565 | 100 | 69 |
| 3A | Cr-Oxyfluoride | 11 | 420 | 69 | 47 |
| 3B | Cr-Oxyfluoride | 10 | 440 | 78 | 43 |
| 4A | Carbon | 10 | 500 | 32 | 96 |
| 4B | Carbon | 11 | 550 | 69 | 86 |
| 4C | Carbon | 12 | 600 | 85 | 76 |
| 5A | 1.5-wt %-Pd/C | 5 | 450 | 56 | 58 |
| 5B | 1.5-wt %-Pd/C | 7 | 475 | 68 | 53 |
| 6A | 4-6-wt %-FeCl$_3$/C | 8 | 250 | 42 | 49 |
| 6B | 4-6-wt %-FeCl$_3$/C | 8 | 300 | 59 | 37 |

What is claimed is:
1. A process for the synthesis of 2,3,3,3-tetrafluoropropene comprising:
(a) reacting hydrogen fluoride (HF) at a temperature of from about 0° C. to about 250° C. and at a pressure of from about 500 to about 1000 psig with a compound of formula (IIA)

$$CH_2X^2CX^2=CX^2X^2 \qquad (IIA)$$

to produce an intermediate reaction product comprising from about 40 wt. % to about 70 wt. % $CF_3CHFCH_2F$, and (b) exposing at least a portion of said intermediate reaction product to reaction conditions effective to convert at least a portion of said $CF_3CHFCH_2F$ to a compound of formula (IV)

$$CF_3CZ=CH_2 \qquad (IV)$$

wherein each $X^2$ is independently selected from the group consisting of hydrogen, chlorine, bromine, fluorine and iodine, Z is F wherein said exposing step (b) comprises a liquid phase reaction or a vapor phase reaction, wherein the liquid phase reaction comprises contacting at least a portion of said $CF_3CHFCH_2F$ with a potassium hydroxide solution and wherein the vapor phase reaction comprises contacting at least a portion of said $CF_3CHFCH_2F$ with at least one metal-based catalyst selected from the group consisting of Ni-mesh, Ni/C, $Cr_2O_3$, activated carbon, Pd/C, and $FeCl_3$.

2. The process of claim 1 wherein said intermediate reaction product further comprises a compound of formula (III)

$$CF_3CHX^1CH_2X^2 \qquad (III),$$

wherein $X^1$ and $X^2$ are each independently selected from the group consisting of hydrogen, chlorine, bromine, fluorine and iodine, and wherein the compound is not $CF_3CHFCH_2F$.

3. The process of claim 1 wherein said compound of formula (IIA) is $CH_2ClCCl=CCl_2$.

4. The process of claim 1 wherein said reacting step (a) is a catalyzed liquid phase reaction.

5. The process of claim 1 wherein said catalyst comprises $SbCl_5$.

6. The process of claim 1 wherein said exposing step (b) is a liquid phase reaction that involves contacting at least a portion of said $CF_3CHFCH_2F$ with a potassium hydroxide solution and, optionally, a Crown ether.

7. The process of claim 6 wherein said exposing step is at least partially conducted at a temperature of from about 25° C. to about 90° C. and at a pressure of about 100 to about 200 psig.

8. The process of claim 1 wherein said exposing step (b) is a vapor phase reaction that involves contacting at least a portion of said $CF_3CHFCH_2F$ with at least one metal-based catalyst selected from the group consisting of Ni-mesh, Ni/C, $Cr_2O_3$, activated carbon, Pd/C, and $FeCl_3$.

9. The process of claim 8 wherein said metal-based catalyst is at least one of Pd/C or Ni/C.

10. The process of claim 9 wherein said exposing step is at least partially conducted at a temperature of from about 200° C. to about 500° C.

11. A process for the synthesis of 2,3,3,3 tetrafluoropropene comprising:

(a) reacting hydrogen fluoride at a temperature of from about 0° C. to about 250° C. and at a pressure of from about 500 to about 1000 psig with a compound of formula (IIA)

$$CH_2X^2CX^2=CX^2X^2 \qquad (IIA)$$

to produce an intermediate reaction product comprising from about 40 wt. % to about 70 wt. % $CF_3CHFCH_2F$, and (b) exposing at least a portion of said intermediate reaction product to reaction conditions effective to convert said $CF_3CHFCH_2F$ to a compound of formula (IVA)

$$CF_3CF=CH_2 \qquad (IVA),$$

wherein each $X^2$ is each independently selected from the group consisting of chlorine, bromine, fluorine and iodine, wherein said exposing step (b) comprises liquid phase reaction or a vapor phase reaction, wherein the liquid phase reaction comprises contacting at least a portion of $CF_3CHFCH_2F$ with a potassium hydroxide solution and wherein the vapor phase reaction comprises contacting at least a portion of $CF_3CHFCH_2F$ with a metal-based catalyst selected from the group consisting of Ni-mesh, Ni/C, $Cr_2O_3$, activated carbon, Pd/C, and $FeCl_3$.

12. A process for the synthesis of 2,3,3,3-tetrafluoropropene comprising:

(a) reacting hydrogen fluoride (HF) at a temperature of from about 0° C. to about 250° C. and at a pressure of from about 500 to about 1000 psig with a compound of formula (IIA)

$$CH_2X^2CX^2=CX^2X^2 \qquad (IIA)$$

to produce an intermediate reaction product comprising from about 40 wt % to about 70 wt. % $CF_3CHFCH_2F$ and further comprising one or more compounds selected from the group consisting of $CF_3CFClCH_3$; $CF_3CHFCH_2Cl$; and $CF_3CHClCH_2Cl$;

(b) exposing said intermediate reaction product to reaction conditions effective to convert said intermediate reaction product to a compound of formula (IV)

$$CF_3CZ=CH_2 \qquad (IV)$$

wherein each $X^2$ is independently selected from the group consisting of hydrogen, chlorine, bromine, fluorine and iodine, Z is F wherein said exposing step (b) comprises a liquid phase reaction or a vapor phase reaction, wherein the liquid phase reaction comprises contacting the intermediate reaction product with a potassium hydroxide solution and wherein the vapor phase reaction comprises contacting the intermediate reaction product with a metal-based catalyst selected from the group consisting of Ni-mesh, Ni/C, $Cr_2O_3$, activated carbon, Pd/C, and $FeCl_3$.

* * * * *